United States Patent [19]

Scherrer

[11] 4,022,908

[45] May 10, 1977

[54] USE OF CERTAIN 2-NITRO-3-PHENYL-ALKOXYBENZOFU-RANS IN INHIBITING GROWTH OF MICROORGANISMS AND INTERMEDIATES IN THE SYNTHESIS OF SAID BENZOFURANS

[75] Inventor: Robert A. Scherrer, White Bear Lake, Minn.

[73] Assignee: Riker Laboratories, Inc., Northridge, Calif.

[22] Filed: Nov. 3, 1975

[21] Appl. No.: 628,329

Related U.S. Application Data

[62] Division of Ser. No. 446,006, Feb. 26, 1974, Pat. No. 3,927,037.

[52] U.S. Cl. .......................... 424/285; 260/346.2 R
[51] Int. Cl.² ............ A61K 31/345; C07D 307/82; C07D 307/86

[58] Field of Search .............. 260/346.2 R; 424/285

[56] References Cited

OTHER PUBLICATIONS

Royer et al., Bull. Soc. Chim. France, (1961), pp. 939–943.
Domschke, Chem. Abstr., vol. 65, (1966), 12156b.
Vogel, Practical Organic Chem., New York–John Wiley, (1963), pp. 681–682.

*Primary Examiner*—John D. Randolph
*Assistant Examiner*—Bernard Dentz
*Attorney, Agent, or Firm*—Cruzan Alexander; Donald M. Sell; Donald C. Gipple

[57] ABSTRACT

Certain alkoxy-substituted-2-nitro-3-phenylbenzofurans are prepared by the exchange reaction of 2-halo-3-phenylbenzofurans with nitrating agents and are found to be useful antimicrobial agents.

12 Claims, No Drawings

USE OF CERTAIN 2-NITRO-3-PHENYL-ALKOXYBENZOFURANS IN INHIBITING GROWTH OF MICROORGANISMS AND INTERMEDIATES IN THE SYNTHESIS OF SAID BENZOFURANS

BACKGROUND OF THE INVENTION

This invention relates to the synthesis of 2-nitro-3-phenylbenzofurans substituted by one or more lower alkoxy groups on the benzo ring, to the use of these compounds as antimicrobial agents, to antimicrobial compositions containing them and to methods for their preparation.

Stoermer (Berichte 44,1853(1911)) reports the synthesis of 5-methyl-2-nitro-3-phenylbenzofuran and 6-methyl-2-nitro-3-phenylbenzofuran (named as 4 or 5-methyl-1-nitro-2-phenylcumarons) which would differ from the compounds of the present invention in ring substitution. However, it is apparent from the analytical and melting point measurements reported there that Stoermer did not obtain those compounds.

DETAILED DESCRIPTION OF THE INVENTION

The invention relates to compounds of the formula

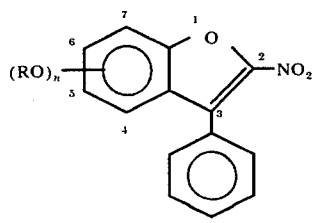

wherein R is lower alkyl of one to six carbon atoms and $n$ is one to three. This invention also relates to the use of these novel compounds as antimicrobial agents and to processes for their preparation.

It has been found that substitution in the 4 position of the 3-phenylbenzofuran ring is less desirable with respect to antimicrobial activity versus gram-negative and gram-positive bacteria. For this reason a preferred subclass of the formula

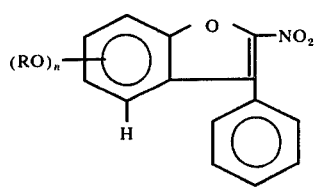

can be designated wherein R and n are as defined hereinabove and H indicates an unsubstituted ring position. Compounds of the invention containing one methoxy group in the position 5, 6 or 7, are found to have good antimicrobial activity, and form a preferred subclass. The most preferred compounds of the invention are 6-methoxy-2-nitro-3-phenylbenzofuran and 6-ethoxy-2-nitro-3-phenylbenzofuran.

The antimicrobial activity of the compounds of the present invention can be demonstrated by the known, standard plate dilution method for bacterial susceptibility to anti-bacterial agents. The culture medium employed permits susceptibility testing of fastidious microorganisms toward antibiotics, sulfonamides and other chemotherapeutic agents. For example, tryptone soy agar (oxoid) of the following composition may be the culture medium.

| | |
|---|---|
| Oxoid tryptone | 15 g. |
| Oxoid Soy peptone | 5 g. |
| Sodium chloride | 5 g. |
| Oxoid agar-agar No. 3 | 15 g. |
| Water | 1 liter | using this test, the compounds of the invention have been found to have a broad spectrum of activity against gram-positive and gram-negative microrganisms.

The compounds of the invention generally maintain activity against microorganisms either in the absence or presence of ten percent horse serum.

The test procedure used to determine activity as employed in connection with the present invention provides information on the amount of a compound required to give complete inhibition, partial inhibition or no inhibition of microbial growth on the agar plates. In the tests, the selected compound is added to the agar medium to give concentrations of zero, one tenth, one, ten and one hundred milligrams per liter. A series of plates with these concentrations is prepared. Ten percent horse serum is added to one series of such plates. Aliquots of broth culture of each of the species of microorganisms are innoculated onto the agar plates containing the various compound concentrations.

The plates are incubated at 37° C. In a ten percent carbon dioxide atmosphere for 18 to 24 hours. The microbial growth on each plate is read visually, and minimal inhibitory concentrations are recorded.

The microorganisms used for this test are:
1. Staphylococcus aureus
2. Bacillus subtilus
3. Pseudomonas aeruginosa
4. Escherichia coli
5. Streptococcus sp.*
6. Aspergillus niger
7. Candida albicans
8. Mima polymorpha
9. Herellea vaginicola
10. Klebsiella pneumoniae
11. Streptococcus fecaelis

*Strain isolated from dental caries in rats or hamsters at the National Institute of Dental Health and grown in PFY or APT agar.

All of the compounds of the invention possess antimicrobial activity towards one or more of the above microorganisms.

It will be understood by those skilled in the art that the species used are representative species, as it would be impractical to screen against all bacteria. It is well known in the art that broad spectrum activity versus certain bacterial classes can be predicted on the activity shown against selected representative bacterial species.

All of the compounds of the invention are active against microorganisms in vitro or topically. In vitro activity is useful in itself, since antimicrobial agents may be used for disinfecting and sterilizing, for example medical and dental equipment, as components of disinfecting solutions. In addition, the preferred compounds of the invention are also active in vivo.

The in vivo antimicrobial activity of a test compound is determined against infections produced by Streptococcus fecaelis and Staphylococcus aureus (Smith). The species used is determined by the in vitro antimicrobial spectrum of the compound. Groups of 5or 0 mice, 18–22 g., are infected intraperitoneally with the test culture. Treatment consists of three oral dosings 1, 6 and 24 hours after infection. All mice are observed for two weeks and deaths recorded at daily intervals. Control groups consist of one infected, non treated group and other infected groups receiving varying dosages of the reference standard. Reference standards are determined by the nature of the compound being screened (sulfonamide, quinoline, antibiotic, etc.). Cephalosporin or ampicillin is generally used.

It is known to the art that antimicrobial agents are used as growth promoters in various animal and bird species. It is inferred from the antimicrobial activity that the compounds of the invention can be used for this purpose also.

It is also sometimes advantageous to combine the compounds of this invention with other antiprotozoal compounds such as coccidiostats, anthelmintics, antifungals, antibiotics, steroids, or antibacterial agents, or to combine more than one compound described herein in a single composition. Such combinations often provide for an active composition more beneficial than either compound alone.

The compounds of the invention are active against protozoa and would be expected to be active against protozoal diseases such an enterohepatitis, amoebic dysentery, turkey blackhead disease and the like, as well as systemic infections, e.g. local endocarditis, descending upper tract kidney infections, wound infections and eye, ear and sinus infections.

Compounds of the invention are active antiparasitics versus Trichomonas sp.

Compounds of the invention are shown by laboratory screening tests to be active versus anaerobic bacteria versus Bacteroides sp. and Clostridium welchii.

Antitubercular activity has been indicated in laboratory tests versus Mycobacterium tuberculosis var. hominis, BCG vaccine strain.

Activity versus Erwinia amylovora, a bacteria causing plant disease, has been shown in laboratory tests.

The acute oral toxicity of the compounds of the invention generally is moderate to low compared with the effective oral dose, and they have a fair to excellent therapeutic ratio. Presently preferred compounds of the invention have a broad spectrum of antimicrobial activity and a good therapeutic ratio ($LD_{50}$/ $ED_{50}$).

The compounds are preferably administered orally as antimicrobial agents but other known methods of administration are contemplated as well, e.g. by subcutaneous injection, intramuscular injection, intravenously, parenterally, topically, and the like. Dosages ordinarily fall within the range of about 1 to 100 mg/kg of body weight of the mammal to be treated although oral dosages are not usually above 50 mg/kg and injection dosages are not usually above 25 mg/kg.

Since the active compounds of the invention are both neutral and stable, they are readily formulated by conventional methods known to the art, e.g. with pharmaceutically acceptable diluents, vehicles, carriers or extending media.

Suitable forms for oral administration include tablets (which may contain anhydrous lactose, microcrystalline cellulose, modified starch, calcium stearate and talc, as well as other pharmaceutically acceptable extending media, diluents, vehicles and conventional compounding agents together with the active antimicrobial agent) and capsules. Liquid formulations, such as solutions or suspensions of the active ingredient in inert carriers, are contemplated for dosage by injection. Suitable carriers and extending media would include water, glucose solution, saline solution, dextran solution and the like.

The compounds of the invention are prepared by several methods starting with known starting materials or using reaction sequences described hereinbelow which start with known starting materials.

Direct nitration of 3-phenylbenzofurans may be used. The use of dinitrogen tetroxide in acetic acid is sometimes advantageous.

Another useful synthetic route utilizes a reaction sequence wherein the first step is a selective and specific halogenation of the 2-position of the benzofuran ring and the second step is selective replacement of the halogen of the aromatic system by a nitro group. In some cases the halogenation is more selective than others, e.g. alkoxy in the 6-position which tends to promote benzo ring halogenation is less desirable than alkoxy in the 7-position.

The halogenation reaction may be bromination or iodination. Bromination is carried out using bromine water or preferably bromine in a suitable solvent such as chloroform or acetic acid. The bromo compound may be isolated or may be used without isolation. Isolation may be carried out by extraction, precipitation by the addition of a solvent such as water which precipitates the product, evaporation of volatile reaction components and the like. Chromatographic purification may be advantageous. Iodination is carried out with molecular iodine in the presence of yellow mercuric oxide in an inert solvent such as benzene.

Selective replacement of the 2-halo substituent is carried out using selected nitrating agents, such as sodium nitrite with 70% nitric acid solution in acetic acid, dinitrogen tetroxide in an inert solvent such as chloroform or acetic acid or a mixture of sodium nitrite and other strong acids in acetic acid. In the first instance preferably about two moles of sodium nitrite per mole of benzofuran is included and one to three milliliters of 70 % nitric acid per gram of nitrite is used. Another component of the nitration reagent is glacial acetic acid as solvent. About four to twenty milliliters of acetic acid per gram of 2-halobenzofuran derivative is used, depending on its solubility. It is desired to maintain the dissolution of the 2-halobenzofuran derivative, and the amount of acetic acid and the reaction temperature is adjusted to achieve this result readily. The reaction temperature is about 25° to 100° C., and preferably about 60° to 80° C. to aid removal of bromine produced.

It has been found that a mixture of sodium nitrite, nitric or sulfuric acid and acetic acid in the presence of an olefin will also nitrate the 2-halobenzofuran derivatives successfully in the 2-position, and this is a preferred procedure. The 2-halobenzofuran derivative is dissolved in acetic acid to maintain solution (up to 20 ml per gram required) and concentratred nitric or sulfuric acid is added. Sodium nitrite is then added, from two to five moles of nitrite per mole of benzofuran derivative being used. The amount of concentrated nitric or sulfuric acid added is from one to three milliliters per gram of the sodium nitrite. The reaction temperature is about 10° to 100° C. Presumably other metal nitrites than sodium nitrite such as potassium nitrite are equivalent and could be used alternatively.

A combination of dinitrogen tetroxide in an inert solvent in the presence of an alkene is the presently preferred nitration method. Acetic acid is a preferred solvent because it dissolves the 2-halobenzofuran derivative and is inert to dinitrogen tetroxide. Two to five liters of acetic acid per mole of benzofuran derivative are generally used. At least one mole of dinitrogen tetroxide per mole of benzofuran is used. The exact amount depends on the rate of reaction desired, the extent of volatilization and other physical losses and the amount of competitive additions to the added olefin. The temperature of these reactions is generally about 0° to 80° C., about 10° to 80° C. for bromine exchange and about 0° to 25° C. for iodine exchange.

An alkene is preferably used when the 2-halobenzofuran derivative is a bromo derivative, since it removes the elements of $BrNO_2$ and minimizes bromination as a side reaction. Cyclohexene -4-carboxylic acid or itaconic acid is satisfactory for this use. Preferably one mole of alkene per mole of dinitrogen tetroxide is used.

The olefin is chosen to be less reactive to $N_2O_4$ than the benzofuran but more reactive to $BrNO_2$ than is the benzofuran. An acidic olefin, e.g. cyclohexene-4-carboxylic acid or itaconic acid is advantageous with the neutral products of this invention.

When 2-iodobenzofurans are used, only one-half mole of $N_2O_4$ is theoretically required in the absence of olefin. Olefin is not required since the iodine is generally unreactive to the benzofuran under the conditions used.

In some cases it is preferred for the compounds of the present invention to utilize novel classes of intermediates, i.e. hydroxy-3-phenylbenzofurans (I) are first prepared. These are then reacted with a suitable acid chloride (e.g. benzoyl chloride) to prepare the derivative (II) in which the hydroxy group is protected by an easily removed blocking group e.g. benzoyl. These blocked hydroxy-3-phenylbenzofurans are conveniently halogented in the 2-position to form another class of intermediates (III) which are then nitrated to provide novel blocked hydroxy-2-nitro-3-phenylbenzofurans (IV). Then the blocking group is removed (V) and the hydroxy group is alkylated e.g. with an alkyl iodine to give an alkoxy substituent. These novel classes of intermediate compounds form aspects of the present invention and can be represented by the following formulas:

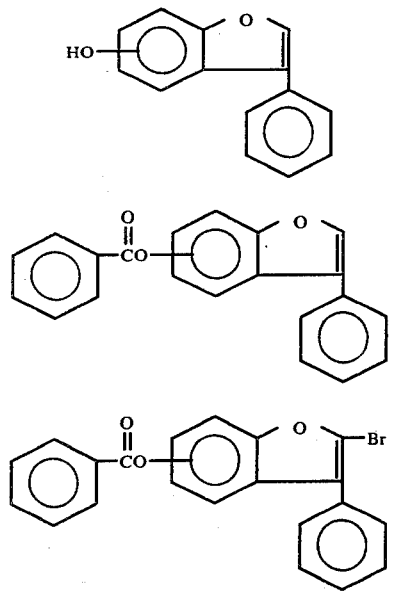

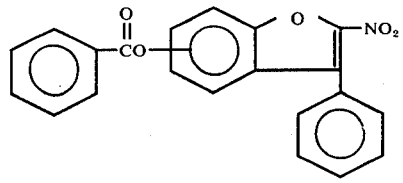

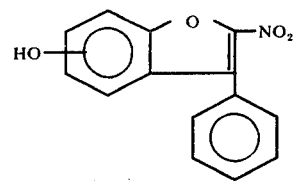

The synthetic processes described hereinabove are illustrative of procedures useful for obtaining the compounds of this invention but are not intended to be limiting. The following examples will more fully illustrate the preparation of the compounds of the invention using these processes.

EXAMPLE 1

A stirred mixture of 500 g (2.19 mole) of 2-hydroxy-4-methoxybenzophenone, 280 g (2.29 mole) of ethyl chloroacetate, 463 g (3.35 mole) of potassium carbonate and 10 g of potassium iodide in 1.75 l. of acetone is heated to its reflux temperature and maintained at reflux for about 18 hours. The mixture is cooled to about 25° C. and filtered. The residue is washed with benzene. The washings and filtrate are combined and evaporated to provide an oil which solidifies gradually to the desired product in crude form, ethyl (2-benzoyl-5-methoxyphenoxy) acetate.

A stirred mixture of 714 g (2.27 mole) of crude ethyl (2-benzoyl-5-methoxyphenoxy) acetate and 61.3 g (1.14 mole) of sodium methoxide in 4.6 l. of ethanol is heated to its reflux temperature and maintained at reflux for about three hours. After sitting about sixteen hours at room temperature the mixture is filtered. The residue is washed with ethanol. The washings and filtrate are combined to give an ethanolic solution of ethyl 6-methoxy-3-phenylbenzofuranyl-2-carboxylate.

To the ethanolic solution of ethyl 6-methoxy -3-phenyl-benzofuranyl-2-carboxylate is added 500 g of sodium hydroxide in one liter of ethanol and the mixture is heated to its reflux temperature and maintained at reflux for four hours. The solid is separated by filtration, washed with ethanol, then dissolved in 10 l. of hot water. The aqueous solution is treated with decolorizing charcoal, then acidified to pH one with concentrated hydrochloric acid. The product is collected by filtration and dried to give 6-methoxy-3-phenylbenzofuranyl-2-carboxylic acid, m.p. 201°–205° C. The structure is confirmed by infrared spectral analysis.

A mixture of 115 g (0.43 mole) of 6-methoxy-3-phenylbenzofuranyl -2-carboxylic acid and 11.5 g of copper powder in 575 ml of quinoline is heated at 225° to 235° C. for 1.5 hours. The mixture is allowed to cool to about 25° C. and 825 ml of 6N-hydrochloric acid is added to give pH one. The mixture is then extracted with diethyl ether. The extracts are washed with water, and saturated sodium chloride solution, then dried. The extracts are then evaporateed to provide a residue which is disolved in 2 l. of hot hexane, treated with decolorizing charcoal and slowly cooled with an ice bath to about 10° C. The solid collected by filtration is 6-methoxy-3-phenylbenzofuran, m.p. 38°to 40° C. The structure is confirmed by infrared spectral analysis.

To a stirred solution of 30 g (0.134 mole) of 6-methoxy-3-phenylbenzofuran in 150 ml of acetic acid is added 30 ml of 47% stabilized hydroiodic acid. The mixture is heated to its reflux temperature and maintained at reflux for seven hours. A precipitate is obtained which is separated by filtration, rinsed with water and dried to provide crude 6-hydroxy-3-phenylbenzofuran, m.p. 138°–143° as an off-white powder.

Additional product is obtained by pouring the acetic acid filtrate in water, collecting the solid, dissolving in diethyl ether and extracting the ether layer with cold 5% sodium hydroxide solution. The basic extracts are neutralized with cold 10% hydrochloric acid to precipitate crude solid product.

Using the method of Example 1 and starting with 2-hydroxy-3-methoxybenzophenone, 2-hydroxy-5-methoxybenzophenone or 2-hydroxy-6-methoxybenzophenone one prepares 7-hydroxy-3-phenylbenzofuran, 5-hydroxy-3-phenylbenzofuran and 4-hydroxy-3-phenylbenzofuran, respectively.

EXAMPLE 2

To a stirred solution of 23.0 g (0.110 mole) of 6-hydroxy-3-phenylbenzofuran in 400 ml of benzene is added 23 g (0.23 mole) of calcium carbonate, then the mixture is heated to its reflux temperature and maintained at reflux while adding dropwise 15.5 g (0.110 mole) of benzoyl chloride over one hour. After refluxing for about nine hours 8.7 g (0.11 mole) of pyridine in 25 ml of benzene is added dropwise, then 1.6 g of benzoyl chloride in 10 ml of benzene is added and finally an additional 8.7 g (0.11 mole) of pyridine is added. A total of 15 hours of refluxing is used. After sitting for about 16 hours the mixture is filtered, the filtrate is washed with 2N hydrochloric acid, water and saturated sodium chloride solution and dried. After concentration an off-white residue is obtained. Recrystallization from cyclohexane gives 6-(3-phenylbenzofuranyl)- benzoate as an off-white powder, m.p. 106°–114° C.

To a stirred solution of 31.3 g (0.10 mole) 6-(3-phenylbenzofuranyl) benzoate in 200 ml of dichloromethane is added 10 g of sodium acetate, then dropwise 16 g (0.10 mole) of bromine in 25 ml of dichloromethane. After stirring about 22 hours the mixture is filtered, washed with water and dried. Evaporation gives the desired product, 6-(2-bromo-3-phenylbenzofuranyl) benzoate.

To a stirred solution of 20 g (0.051 mole) of 6-(2-bromo-3-phenylbenzofuranyl)benzoate in 300 ml of acetic acid at 40° C. is added 9.6 g (0.076 mole) of cyclohexene-4-carboxylic acid, then dropwise 7.0 g (0.076 mole) of dinitrogen tetraoxide in 25 ml of acetic acid over two hours. A yellow solid precipitates and is separated by filtration and washed with acetic acid and water. Recyrstallization from benzene-hexane gives yellow needles of 6-(2-nitro-3-phenylbenzofuranyl)-benzoate, m.p. 184°–186° C.

| Analysis: | %C | %H | %N |
|---|---|---|---|
| Calculated for $C_{21}H_{13}NO_5$: | 70.2 | 3.65 | 3.9 |
| Found: | 70.4 | 3.8 | 3.8 |

A mixture of 13.0 g (0.036 mole) of 6-(2-nitro-3-phenylbenzofuranyl)benzoate, 10 g (0.10 mole) of N-methylpiperazine and 250 ml of benzene is heated to its reflux temperature and maintained at reflux for 2 hours. The mixture is then diluted and extracted with diethyl ether. The ether extracts are washed with hydrochloric acid, water and saturated sodium chloride solution and dried. Evaporation provides a residue which when recrystallized from benzene gives a yellow powder, 6-hydroxy-2-nitro-3-phenylbenzofuran, m.p. 201°–203° C. dec.

| Analysis: | %C | %H | %N |
|---|---|---|---|
| Calculated for $C_{14}H_9NO_4$: | 65.9 | 3.6 | 5.5 |
| Found: | 65.9 | 3.7 | 5.3 |

Using the method of Example 2 and starting with 7-hydroxy-3-phenylbenzofuran; 5-hydroxy-3-phenylbenzofuran and 4-hydroxy-3-phenylbenzofuran one prepares 7-hydroxy-2-nitro-3-phenylbenzofuran, 5-hydroxy-2-nitro-3-phenylbenzofuran and 4-hydroxy-2-nitro-3-phenylbenzofuran.

EXAMPLE 3

To a suspension of 0.34 g (0.008 mole) of sodium hydride in 45 ml of glyme is added dropwise a solution of 2.0 g (0.008 mole) of 6-hydroxy-2-nitro-3-phenylbenzofuran in 20 ml of glyme. To this suspension is added 16 g (0.010 mole) of ethyl iodide and the mixture is heated to its reflux temperature and maintained at reflux for 5 hours. After cooling to 25° C. an additional 0.1 g of sodium hydride and 5ml of ethyl iodide are added and the mixture is refluxed for about three hours. The mixture is poured into water and extracted with diethyl ether. The extracts are washed with water and saturated sodium chloride solution and dried. Concentration of the extracts provides a residue which is recrystallized from aqueous ethanol to provide yellow needles of 6-ethoxy-2-nitro-3-phenylbenzofuran, m.p. 109°–111° C.

| Analysis: | %C | %H | %N |
|---|---|---|---|
| Calculated for $C_{16}H_{13}NO_4$: | 67.8 | 4.63 | 4.94 |
| Found: | 67.3 | 4.7 | 4.9 |

EXAMPLE 4

To a suspension of 0.34 g (0.008 mole) of sodium hydride in 45 ml of glyme is added dropwise a solution of 2.0 g (0.008 mole) of 6-hydroxy-2-nitro-3-phenylbenzofuran in 20 ml of glyme. To this suspension is added 21 g (0.010 mole) of n-hexyl iodide. After stirring for 2 hours the mixture is heated to its reflux temperature and maintained at reflux for about 27 hours. The mixture is allowed to cool for about 16 hours, poured into water and extracted with diethyl ether. The extracts are washed with water and saturated sodium chloride solution and dried. The dried extracts are concentrated to provide a dark oil residue. The residue is chromatographed on silica gel, eluting with carbon tetrachloride, then 1:1 chloroform :carbon tetrachloride to provide middle fractions which are determined by infrared spectral analysis and nuclear magnetic resonance spectral analysis to contain the desired product, 6-n-hyxyloxy-2 -nitro-3-phenylbenxofuran as an orange oil.

EXAMPLE 5

To a solution of 25 g (0.112 mole) of 6-methoxy-3-phenylbenzofuran in 400 ml of dichloromethane is added over 1 hour dropwise with stirring 17.9 g (0.112 mole) of bromine in 20 ml of dichloromethane. The solution is washed with 200 ml of 10% aqueous sodium acetate, dried and evaporated to provide 2-bromo-6-methoxy-3-phenylbenzofuran as a dark oil.

To a solution of 33.9 g (0.112 mole) of 2-bromo-6-methoxy-3-phenylbenzofuran in 1 l. of acetic acid is added 21.2 g (0.168 mole) of cyclohexene-4-carboxylic acid, then 15.5 g (0.168 mole) of dinitrogen tetraoxide in 20 ml of acetic acid is added dropwise over 1.5 hours. After 3 additional hours the mixture is poured into cold water to give a yellow gum. The mixture is treated with diethyl ether and the solid residue is collected by filtration. This residue is recrystallized from aqueous ethanol, cyclohexane and ethanol to provide yellow solid 6-methoxy-2-nitro-3-phenylbenzofuran, m.p. 100°–106° C., containing 20 % 7-bromo-6-methoxy-2-nitro-3-phenylbenzofuran.

EXAMPLE 6

A mixture of 1 mole of 2-methoxyphenol and 1 mole of potassium carbonate in acetone is heated at reflux while adding 1 mole of alpha-bromoacetophenone. The mixture is refluxed for several hours to provide alpha-(2-methoxyphenoxy)acetophenone.

To a stirred, heated (60° C.) 178 g batch of polyphosphoric is added 25 g (0.103 mole) of alpha-(2-methoxyphenoxy)-acetophenone. After about 45 minutes the mixture is poured into cold water. The aqueous solution is extracted into diethyl ether, the extracts are washed with water and saturated sodium chloride solution and dried. Evaporation provides a residue which is dissolved in 1:1 chloroform-hexane and eluted through a silica gel column with this solvent mixture. Early fractions are 7-methoxy-3-phenylbenzofuran.

To a stirred solution of 5.3 g (0.024 mole) of 7-methoxy-3-phenylbenzofuran in 200 ml of acetic acid is added dropwise 3.3 g (0.036 mole) of dinitrogen tetroxide in 20 ml of acetic acid. After about 90 minutes the mixture is poured into cold water, precipitating a gum which is isolated by filtration and dissolved in diethyl ether. The ether solution is washed with water and saturated sodium chloride solution and dried. Evaporation gives a residue which is dissolved in chloroform and eluted through a silica gel column with chloroform. Early fractions are a yellow solid which is recrystallized from ethanol to give yellow crystals of 7-methoxy-2-nitro-3-phenylbenzofuran, m.p. 160°–161° C.

| Analysis: | %C | %H | %N |
|---|---|---|---|
| Calculated for $C_{15}H_{11}NO_4$: | 66.9 | 4.12 | 5.2 |
| Found: | 67.0 | 4.3 | 5.1 |

EXAMPLE 7

Using the procedure described in Example 3 and starting with 5-hydroxy-2-nitro-3-phenylbenzofuran and isopropyl iodide one obtains 5-isopropoxy-2-nitro-3-phenylbenzofuran.

EXAMPLE 8

Using the methods of Examples 1 and 5 and starting with 2-benzoyl-4,5,6-trimethoxyphenol and ethyl chloroacetate one obtains 3-phenyl-2-nitro-5,6,7-trimethoxybenzofuran.

EXAMPLE 9

Using the methods of Examples 1 and 5 and starting with 2-benzoyl-5,6-dimethoxyphenol and ethyl chloroacetate one obtains 6,7-dimethoxy-3-phenyl-2-nitrobenzofuran.

EXAMPLE 10 EXAMPLE

Using the methods of Examples 1 and 5 and starting with 2-benzoyl-4,6-dimethoxyphenol and ethyl chloroacetate one obtains 5,7 -dimethoxy-3-phenyl-2-nitrobenzofuran.

The following example is used to illustrate the antimicrobial activity of some of the compounds of the invention against selected microorganisms. The test used is the standard plate dilution method described hereinabove.

Example 11

| Com- pound of Example No. | Concentration at which complete inhibition is noted (mcg/ml) | | | |
|---|---|---|---|---|
| | Streptococcus sp. | | Staphylococcus aureus | |
| | Serum free | With serum | Serum free | With serum |
| 3 | 1 | 10 | 1 | 100 |
| 5 | 1 | 10 | 1 | 1 P |
| 6 | 10 | 10 | 10 | 1 |

| Com- pound of Example No. | Concentration at which complete inhibition is noted (mcg/ml) | | | | | |
|---|---|---|---|---|---|---|
| | Bacillus subtilis | | E. coli | | Enterococcus | |
| | Serum free | With serum | Serum free | With serum | Serum free | With serum |
| 3 | 1 | 1 | 100 P | 100 P | 1 | 10 |
| 5 | 1 | 1 | 1 | 10 | 1 | 10 |
| 6 | 1 P | 1 | 10 | 1 | 10 | 10 |

P in the tables indicates partial inhibition.

The compound of Example 3 shows activity versus Trichomonas sp. at 1 mcg/ml and also shows activity versus Mycobacterium sp. The compounds of Examples 3, 5 and 6 all show activity versus Clostridium sp. and Bacteroides sp. The compound of Example 5 shows activity versus Erwinia amylovora, Aspergillus niger and Candida albicans.

What is claimed is:

1. A method for arresting or inhibiting the growth of microorganisms comprising contacting said microorganisms with a compound of the formula

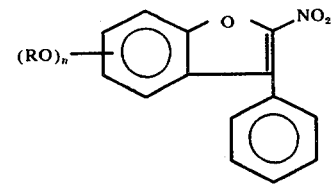

wherein each R is an alkyl group containing from one to six carbon atoms and n is 1–3, in an amount sufficient to inhibit the growth of said microorganisms.

2. A method according to claim 1 wherein the compound is of the formula

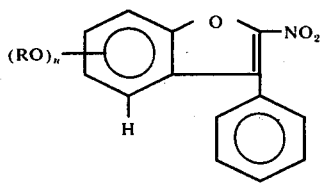

wherein each R is an alkyl group containing from one to six carbon atoms and n is 1–3.

3. A method according to claim 2 wherein n is 1.
4. A method according to claim 1 wherein the compound is 6-ethoxy-2-nitro-3-phenylbenzofuran.
5. A method according to claim 1 wherein the compound is 6-n-hexyloxy-2-nitro-3-phenylbenzofuran.
6. A method according to claim 1 wherein the compound is 6-methoxy-2-nitro-3-phenylbenzofuran.
7. A method according to claim 1 wherein the compound is 7-methoxy-2-nitro-3-phenylbenzofuran.
8. An antimicrobial composition comprising an antimicrobially effective amount of a compound of the formula

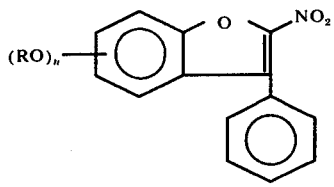

wherein each R is an alkyl group containing from one to six carbon atoms and n is 1–3, dispersed in a pharmaceutically acceptable extending medium.

9. A compound of the formula

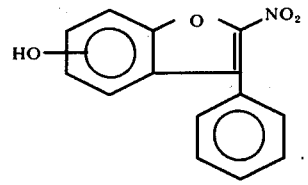

10. A compound of the formula

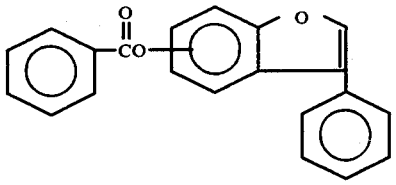

11. A compound of the formula

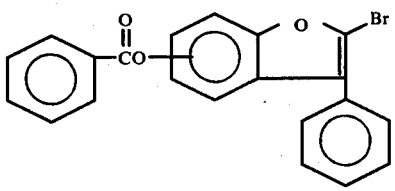

12. A compound of the formula

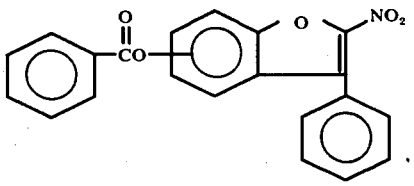

* * * * *